US009918818B2

(12) United States Patent
Khamis et al.

(10) Patent No.: US 9,918,818 B2
(45) Date of Patent: *Mar. 20, 2018

(54) IMPLANT SYSTEMS WITH TENSIONING FEEDBACK

(71) Applicant: Boston Scientific Scimed, Inc., Maple Grove, MN (US)

(72) Inventors: Chaouki A. Khamis, Edina, MN (US); Shawn M. Wignall, Woodbury, MN (US); David J. Kupiecki, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/153,705

(22) Filed: May 12, 2016

(65) Prior Publication Data

US 2016/0256251 A1 Sep. 8, 2016

Related U.S. Application Data

(63) Continuation of application No. 13/520,068, filed as application No. PCT/US2010/062477 on Dec. 30, 2010, now Pat. No. 9,364,308.

(60) Provisional application No. 61/291,238, filed on Dec. 30, 2009.

(51) Int. Cl.
*A61F 2/00* (2006.01)

(52) U.S. Cl.
CPC .... *A61F 2/0045* (2013.01); *A61F 2250/0097* (2013.01)

(58) Field of Classification Search
CPC .............. A61F 2/0045; A61F 2/0063; A61F 2002/0888; A61F 2250/0087; A61F 2250/0078; A61F 2250/0018
See application file for complete search history.

(56) References Cited

U.S. PATENT DOCUMENTS

2008/0177132 A1* 7/2008 Alinsod ................ A61F 2/0045
600/37
2008/0196729 A1* 8/2008 Browning ............. A61F 2/0045
128/834

OTHER PUBLICATIONS

Tsuchihara et al., Development of Polymer films that change color in response to tension. National Institute of Advanced Industrial Scinece and Technology. Press Release Nov. 17, 2008. Retrieved on Jul. 22, 2016. Retrieved from internet: http://www.aist.go.jp/aist_e/latest_research/2008/20081117/20081117.html.*

* cited by examiner

*Primary Examiner* — Christine H Matthews
*Assistant Examiner* — Joshua D Lannu
(74) *Attorney, Agent, or Firm* — Brake Hughes Bellermann LLP

(57) ABSTRACT

Pelvic or other types of implants are provided that can include tensioning feedback components or portions, such as color changing polymer materials, such as polyacetylene. The color changing polymer can be included with, coated on or otherwise provided with a portion of slings or implant devices to provide targeted feedback to the user or physician of the tension applied to a particular device. A first color can be used to indicate a first (initial) tension or compression stage, and a second color can be used to indicate tensioning of the device beyond a predefined threshold.

20 Claims, 3 Drawing Sheets

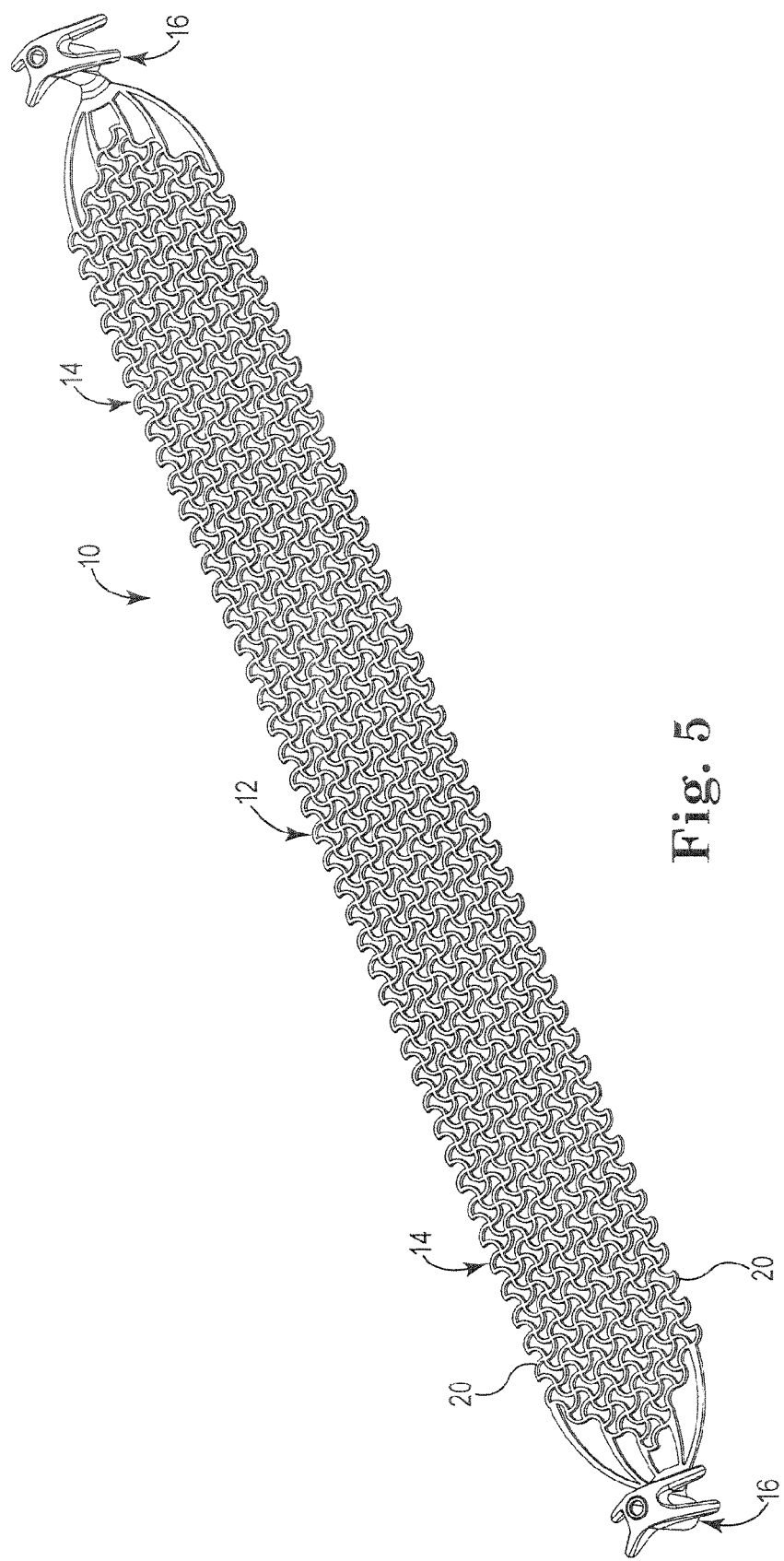

US 9,918,818 B2

IMPLANT SYSTEMS WITH TENSIONING FEEDBACK

PRIORITY

This Application is a Continuation of U.S. patent application Ser. No. 13/520,068, filed Sep. 13, 2012, which is a Section 371 National Stage Application of International PCT Application No. PCT/US10/62477, filed Dec. 30, 2010, which claims priority to and the benefit of U.S. Provisional Application No. 61/291,238, filed Dec. 30, 2009; with each of these identified applications being fully incorporated herein by reference.

FIELD OF THE INVENTION

The present invention relates generally to surgical methods and apparatus and, more specifically, to surgically implantable mesh or sling devices with tensioning feedback features, portions or components.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective implantable mesh that can be used to treat incontinence, and/or pelvic organ prolapse and other conditions.

SUMMARY OF THE INVENTION

The present invention describes pelvic implants and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Embodiments of the implants can include tensioning feedback components or portions, such as color changing polymer materials.

Such color changing polymer material, such as polyacetylene, can be included with, coated on or otherwise provided with a portion of slings or implant devices to provide targeted feedback to the user or physician of the tension applied to a particular device. A first color can be used to indicate a first tension or compression stage, and a second color can be used to indicate tensioning of the device beyond a predefined threshold. In certain embodiments, the color changing polymer is capable of returning to the first color upon elimination of the tension and return of the device portion to the original compression stage. As such, the color changing polymer can be reversible to provide a very useful and real-time indicator of tension and compression on the implant device or device portion.

The color changing polymer can be used to construct all or a part of an implant device (e.g., prolapse mesh, incontinence sling, etc.). In those embodiments where the color changing polymer is utilized to construct only part of the implant device, the polymer can be included with or used to define edges, end portions and other specific device portions typically under tension, or where tension is relative to the implants effectiveness, support functioning, and performance. In certain embodiments, the color changing polymer is provided as a coating on particular implant portions, or defines one or more filaments or members defining the implant or mesh device.

BRIEF DESCRIPTION OF THE DRAWINGS

FIG. 5 is a perspective view of an elongate sling implant provided with a color changing polymer in accordance with embodiments of the present invention.

DETAILED DESCRIPTION OF PREFERRED EMBODIMENTS

Figure 1:
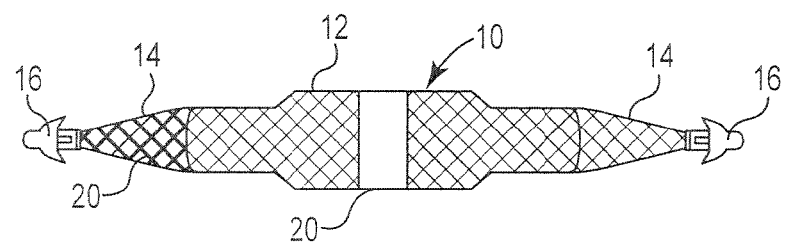
FIG. 1 shows a top view of an elongate sling implant provided with a color changing polymer in accordance with embodiments of the present invention.
Figure 2:
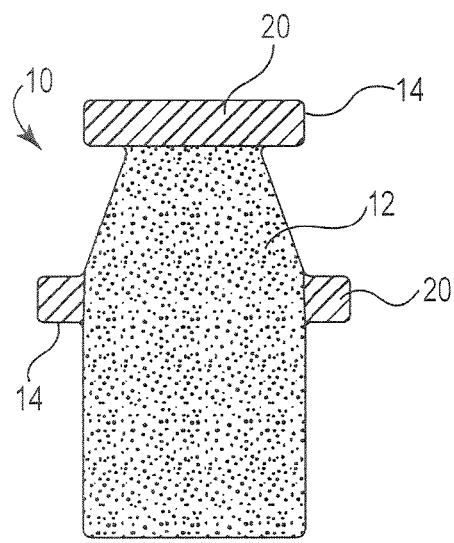
FIGS. 2-4 show a top view of pelvic implants (e.g., prolapse repair) provided with a color changing polymer in accordance with embodiments of the present invention.
Figure 3:
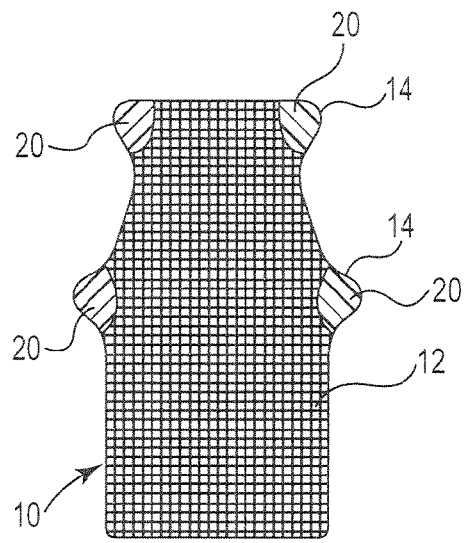
Figure 4:
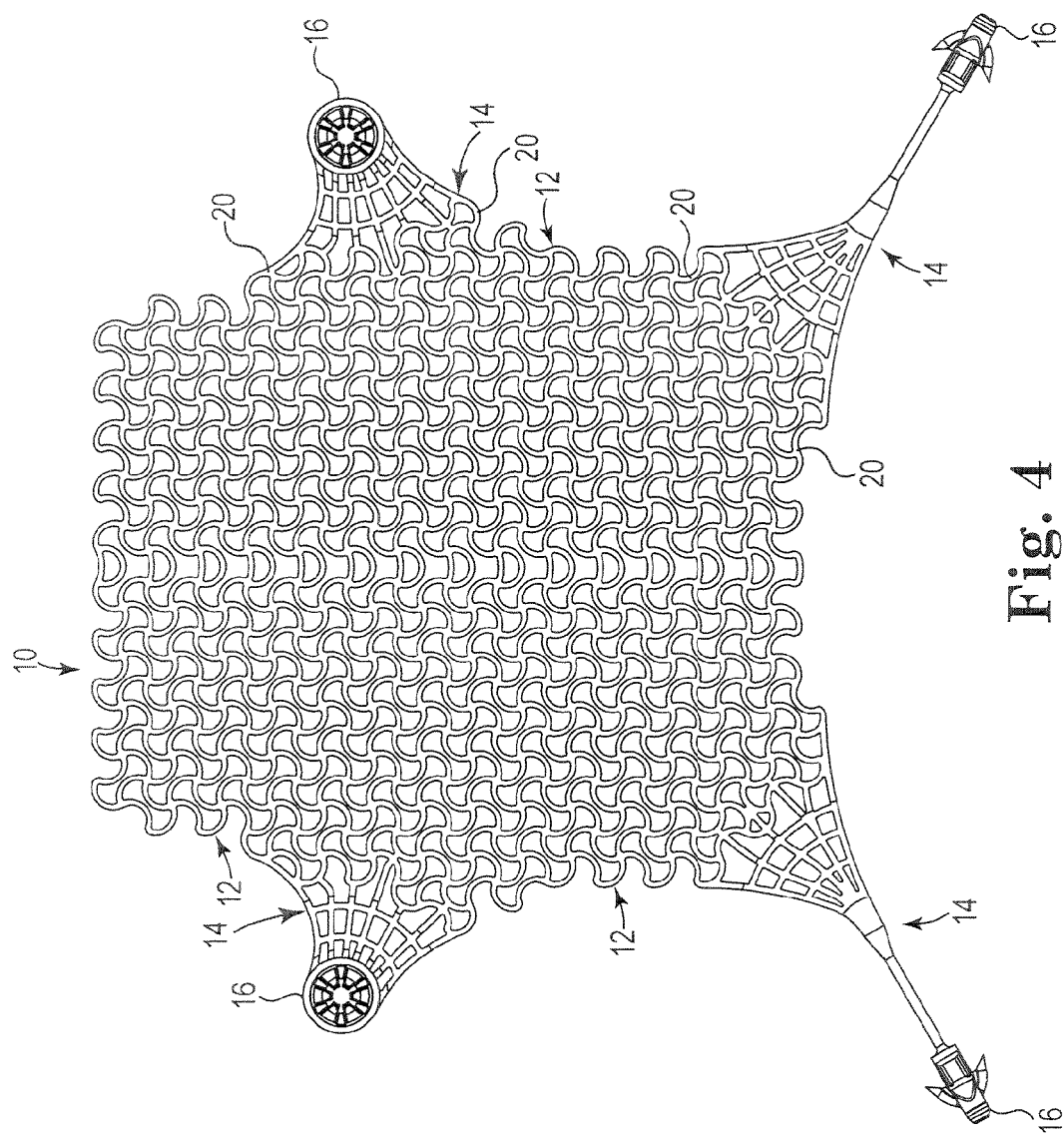

Referring generally to FIGS. 1-5, various embodiments of implantable implant or mesh systems 10 and methods are shown. In general, the implant systems 10 can include a support portion 12 and extension portions 14. Further, anchors 16 or other fixation devices can be included at one or more of the extension portions 14. Various portions of the implant systems 10 can be constructed of polymer materials, such as a thin film or sheet material of polypropylene, polyethylene, fluoropolymers or like compatible materials. The implant systems 10 can be employed to treat incontinence, pelvic prolapse, or like conditions or defects. Various embodiments can be further employed to treat hernias, orthopedic conditions, and other health and wellness issues or problems.

The various implants 10 or systems, features and methods detailed herein are envisioned for use with many known implant and repair systems (e.g., for male and female), features and methods, including those disclosed in U.S. Pat. Nos. 7,500,945, 7,407,480, 7,351,197, 7,347,812, 7,303, 525, 7,025,063, 6,691,711, 6,648,921, and 6,612,977, International Patent Publication Nos. WO 2008/057261 and WO 2010/027796 WO 2007/097994, and U.S. Patent Publication Nos. 2010/0261955, 2002/0151762 and 2002/0147382. Accordingly, the above-identified disclosures are fully incorporated herein by reference in their entirety.

In one embodiment of the implant slings or prolapse systems, a unique color changing polymer 20, film, material or coating, is used to construct or is otherwise incorporated with at least a portion of the sling or implant system 10 to provide a change in colors of the material upon defined tension or compression loads. Molding, extrusion, die casting, weaving and like manufacturing or implant formation methods are envisioned for providing the polymer 20 with one or more portions of the implants 10. The shaded or bold areas or portions in the implants of the figures are generally used to indicate the presence of the color changing polymer 20. Indication of the polymer 20 in specific locations or portions of the implants 10 is for demonstrative purposes only. The polymer 20 can be included or provided with the implants 10 at any portion, component or area where tension or compression feedback is desired. In certain embodiments, the entire construct of the implant 10 (portions 12, 14) can include the polymer 20, or be constructed of the polymer 20.

The polymer 20 can be a known polyacetylene (or other known materials adapted to change colors in response to changes in applied tension) that includes properties whereby the polymer will change color under tension or compression. Such color changing polymer material, such as polyacetylene, can be included with, coated on or otherwise provided with a portion of slings or implant devices to provide targeted feedback to the user or physician of the tension applied to a particular device.

As research has indicated, polymerization of acetylene substituted with a substituted phenyl group using [Rh(norbornadiene)Cl]2 as a catalyst. Measurement of the ultraviolet-visible absorption spectrum may increase in absorption from approximately 500 to 600 nm. Removal of the tension and contracting the film can lead to the return of the color of the film from red to yellow, such that the change in color due to stretching and contracting is reversible. Disclosure of such details can be found in *Development of Polymer Films that Change Color in Response to Tension: Easy visualization of mechanical force*, National Institute of Advanced Industrial Science and Technology (AIST) Press Release, Oct. 7, 2008, which is hereby incorporated herein in its entirety.

A first color (e.g., yellow) can be used to indicate a first tension or compression state, with the polymer 20 at an initial non-tensioned condition. A second color (e.g., red) can be used or triggered to indicate tensioning of the device beyond a predefined threshold. In certain embodiments, the color changing polymer 20 is capable of returning to the first color upon elimination of the tension and return of the device portion to the original compressed or non-tensioned condition. As such, the color changing polymer 20 can be reversible to provide a very useful and real-time indicator of tension and compression on the implant device or device portion.

The color changing polymer 20 can be used to construct all or a part of the implant device 10 (e.g., prolapse mesh, incontinence sling, etc.). In those embodiments where the color changing polymer 20 is utilized to construct only part of the implant device (e.g., FIGS. 2-3), the polymer can be included with or used to define edges, end portions and other specific device portions typically under tension, or where tension is relative or important to the implants effectiveness, support functionality, and performance.

In certain embodiments, the color changing polymer 20 is provided as a coating on particular implant portions. In other embodiments, the polymer 20 is provided with or defines one or more filaments, struts or like members of a mesh implant. As shown generally in FIGS. 1, and 4-5, the polymer 20 filaments or struts can be provided at any select portion or section of the corresponding implant 10.

In certain embodiments, a strip of such polymer 20 can be incorporated with an implant sheath or sleeve, such as those disclosed in the previously-incorporated references. The polymer 20 can be incorporated along a longitudinal length, transversely, or a combination thereof.

When the sling or implant is tensioned, the polymer 20 is also placed under tension and will change color. The color change (which is generally reversible) provides instant feedback to the user as to the level of tensioning achieved. The color level can be developed and validated to provide implanting physicians with a consistent level of tensioning and a highly effective level of tensioning upon deployment of the sling or implant. These tensioning colors can be calibrated to correspond to predefined tensioning levels in accordance with specific applications of the present invention. Further, each color utilized with the tensioning feedback features can be calibrated or noted to define a specific level of tension to promote accuracy, uniformity and consistency across applications or uses.

Further, accessories adapted for interfacing or use with a sling or implant device 10, such as a clamp or grasper, insertion tool or needle, anchors, sutures, eyelets, grommets, to name a few, can include color changing polymer materials integrated or provided therewith. The systems 10, their various components, structures, features, materials and methods may have a number of suitable configurations as shown and described in the previously-incorporated references. Various methods and tools for introducing, deploying, anchoring and manipulating implants to treat incontinence and prolapse as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. An implant device for treating prolapse in a patient, comprising:
    a central support portion;
    two or more extension portions extending from the central portion and constructed of a mesh material; and
    a color changing polymer portion provided with a plurality of mesh filaments of each of the two or more extension portions, and wherein the color changing polymer portion is adjacent to the central support portion, wherein the central support portion does not include the color changing polymer portion, with the color changing polymer portion configured to change colors at a pre-defined tensioning feedback level.

2. The implant of claim 1, wherein the color changing polymer portion includes at least a polyacetylene material.

3. The implant of claim 1, wherein the color changing polymer portion is a polymer coating.

4. The implant of claim 1, wherein the color changing polymer portion is directly adjacent to the central support portion, and the color changing polymer portion provides tensioning feedback by displaying a first color in an initial condition.

5. The implant of claim 4, wherein the color changing polymer portion provides tensioning feedback by displaying a second color when placed under tension.

6. The implant of claim 5, wherein the color changing polymer portion returns to the first color when compressed to the initial condition.

7. The implant of claim 1, further including one or more tissue anchors.

8. The implant of claim 1, wherein the implant is generally elongate.

9. The implant of claim 8, wherein the generally elongate implant includes an anchor provided with each of the two or more extension portions.

10. The implant of claim 1, wherein the two or more extension portions includes four arm portions.

11. An implant device for treating prolapse in a patient, comprising:
a central support portion;
two or more anchoring portions constructed at least in part of a mesh material, and extending from the central portion; and
a color changing polymer portion provided with a plurality of mesh filaments of each of the two or more anchoring portions, and wherein the color changing polymer portion is adjacent to the central support portion, wherein the central support portion does not include the color changing polymer portion, with the color changing polymer portion configured to change colors at a pre-defined tensioning feedback level.

12. The implant of claim 11, wherein the color changing polymer portion includes at least a polyacetylene material.

13. The implant of claim 11, wherein the color changing polymer portion is a polymer coating.

14. The implant of claim 11, wherein the color changing polymer portion is directly adjacent to the central support portion, and the color changing polymer portion provides tensioning feedback by displaying a first color in an initial condition.

15. The implant of claim 14, wherein the color changing polymer portion provides tensioning feedback by displaying a second color when placed under tension.

16. The implant of claim 15, wherein the color changing polymer portion returns to the first color when compressed to the initial condition.

17. The implant of claim 11, further including one or more tissue anchors.

18. The implant of claim 17, wherein the one or more tissue anchors includes at least one tissue anchor operably connected to each of the two or more anchoring portions.

19. The implant of claim 11, wherein the implant is generally elongate.

20. The implant of claim 11, wherein the two or more anchoring portions includes four arm portions.

* * * * *